United States Patent [19]
Leib et al.

[11] Patent Number: 5,318,513
[45] Date of Patent: Jun. 7, 1994

[54] CANALICULAR BALLOON FIXATION STENT

[76] Inventors: Martin L. Leib, 4671 Delafield Ave., Riverdale, N.Y. 10471; Peter Michalos, 1029 46th St., Brooklyn, N.Y. 11219

[21] Appl. No.: 950,925

[22] Filed: Sep. 24, 1992

[51] Int. Cl.$^5$ .................... A61M 5/00; A61M 29/02
[52] U.S. Cl. ........................... 604/8; 606/192
[58] Field of Search ............... 604/8, 96, 98, 99, 101, 604/49, 54; 606/192-194, 196

[56] References Cited

U.S. PATENT DOCUMENTS

| | | | |
|---|---|---|---|
| 1,282,881 | 10/1918 | Landis | 606/192 |
| 2,156,260 | 5/1939 | Crothers | 606/192 |
| 2,215,126 | 9/1940 | McMillin | 606/196 |
| 3,675,658 | 7/1972 | Taylor | 604/98 |
| 3,889,685 | 6/1975 | Miller, Jr. et al. | 604/96 |
| 3,937,224 | 2/1976 | Uecker | 604/101 |
| 4,270,541 | 6/1981 | Okamoto et al. | 606/192 |
| 4,658,816 | 4/1987 | Ector, Jr. | 604/264 |
| 4,660,546 | 4/1987 | Herrick et al. | 604/264 |
| 4,915,684 | 4/1990 | MacKeen et al. | 604/264 |
| 5,021,043 | 6/1991 | Becker et al. | 606/192 |

Primary Examiner—John D. Yasko
Assistant Examiner—Frank Wilkens
Attorney, Agent, or Firm—Weingarten, Schurgin, Gagnerbin & Hayes

[57] ABSTRACT

A fixation stent and a method for using the stent to repair canalicular lacerations and to block fluid flow through a canalicular canal are provided The stent includes a flexible tube having a proximal end, a distal end, an inflatable portion in fluid communication with the distal end, and a plug for sealing and anchoring the proximal end within a body canal. In ophthalmic applications, the distal end of the stent is inserted into a punctum of an eyelid and is then urged through the associated canaliculus towards a lacrimal sac at the end of the canaliculus Once inside the lacrimal sac, the balloon is inflated to a diameter greater than the diameter of the canalicular canal, thereby anchoring and sealing the distal end of the stent within the lacrimal sac. A plug is secured within the proximal end of the stent subsequent to the inflation of the balloon, thereby serving to seal the proximal end of the stent The plug includes a portion with a diameter greater than the diameter of the punctum that rests on the margin of the eyelid, thereby anchoring the proximal end of the stent at the margin of the eyelid Although the stent is particularly suited to ophthalmological applications, it can be used in any narrow body canal.

7 Claims, 3 Drawing Sheets

CANALICULAR BALLOON FIXATION STENT

FIELD OF THE INVENTION

The invention relates to stents for intubation of narrow body canals, and particularly to a stent for intubation of the lacrimal outflow system.

BACKGROUND OF THE INVENTION

There are several instances in which it becomes necessary to intubate the lacrimal outflow system of the eye, which includes the punctal openings on the margin of the eyelids, and the respective upper and lower canalicular canals which open to the lacrimal sac.

For example, eye injuries commonly include canalicular lacerations. It is necessary to treat such lacerations to insure that the canaliculus remains functional and intact upon healing so as to allow proper drainage of fluids such as tear flow from the eye.

The prior system used to repair the damaged canaliculus is complicated and unwieldy, requiring much surgical expertise. The prior system requires that the upper and lower canalicular canals be intubated with coated stainless steel probes even if only one canaliculus is damaged. The steel probes are used to introduce the silastic tubing which is left behind and tied in place. The tubing creates an opening in the damaged canicular canal around which the lacerated tissue can be reconstructed. Thus, the undamaged canaliculus is unnecessarily subjected to potential injury. Moreover, the patient must be under general anesthesia in order to pass the steel probes used to introduce the silicone tubing through the lacrimal outflow system.

Furthermore, in the prior system, the tubing can easily be displaced. Such displacement usually requires complicated methods to return the tubing to its correct position.

It is sometimes necessary to occlude the lacrimal outflow system in the treatment of low tear flow or dry eye. In this instance, the lacrimal outflow system is occluded by a plug to block the outflow of tears, thereby relieving the discomfort associated with dry eye.

Prior systems for blocking the canalicular canals include plugs of various types which are inserted through the punctal openings and into the canalicular canals. However the insertion of these plugs is difficult, and the plugs are also easily displaced and must be reinserted frequently. When displaced, an uncomfortable foreign body sensation results. Therefore, these prior plugs are inconvenient for patients who depend upon blockage of the lacrimal outflow system for extended periods of time to relieve the discomfort related to dry eye conditions.

It would be advantageous to have a system for intubating the lacrimal outflow system of the eye which is free of the above-described disadvantages, and provides looser adherence to the lid margin and better anchoring.

SUMMARY OF THE INVENTION

A balloon fixation stent, a method for repairing canalicular lacerations and a method for blocking fluid flow through the lacrimal outflow system is disclosed. The stent of the invention is easy to insert while the patient is under local anesthesia, thereafter remaining firmly in place for extended periods of time.

In one embodiment, the stent includes a flexible tube having a proximal end, a distal end, an inflatable portion in fluid communication with the distal end, and a plug secured to the proximal end. The distal end of the stent is inserted through a punctum of an eyelid, and is then urged through the associated canalicular canal towards the associated lacrimal sac. Once the inflatable portion rests in the lacrimal sac, it is inflated until it has a diameter greater than the diameter of the canalicular canal, thereby anchoring and sealing the distal end of the stent within the lacrimal sac. A plug is secured within the proximal end of the stent after inflation to seal the proximal end of the stent. The plug includes a portion with a diameter greater than the diameter of the punctum opening, the portion resting on the margin of the eyelid so as to anchor the proximal end of the stent.

In a second embodiment, a bicanalicular fixation stent comprises first and second monocanalicular fixation stents, as described in the first embodiment, each monocanalicular fixation stent being inserted into the upper and lower canalicular canals, respectively, and connected at the respective proximal ends via a fixation rod, thereby forming a bicanalicular balloon fixation stent. The fixation rod functions to seal the proximal ends of each respective monocanalicular stent and to anchor each of the stents at the margin of the eyelid. This embodiment can be used when both upper and lower systems are injured, or when it is desirable to block tear flow of both the upper and lower eyelids, such as in cases of severe dry eye Although the stent is particularly suited to ophthalmological applications, it can be used in any narrow body canal.

DESCRIPTION OF THE DRAWINGS

The invention will be more fully understood from the following solely exemplary detailed description taken in conjunction with the accompanying figures in which.

DETAILED DESCRIPTION OF THE INVENTION

Figure 1:
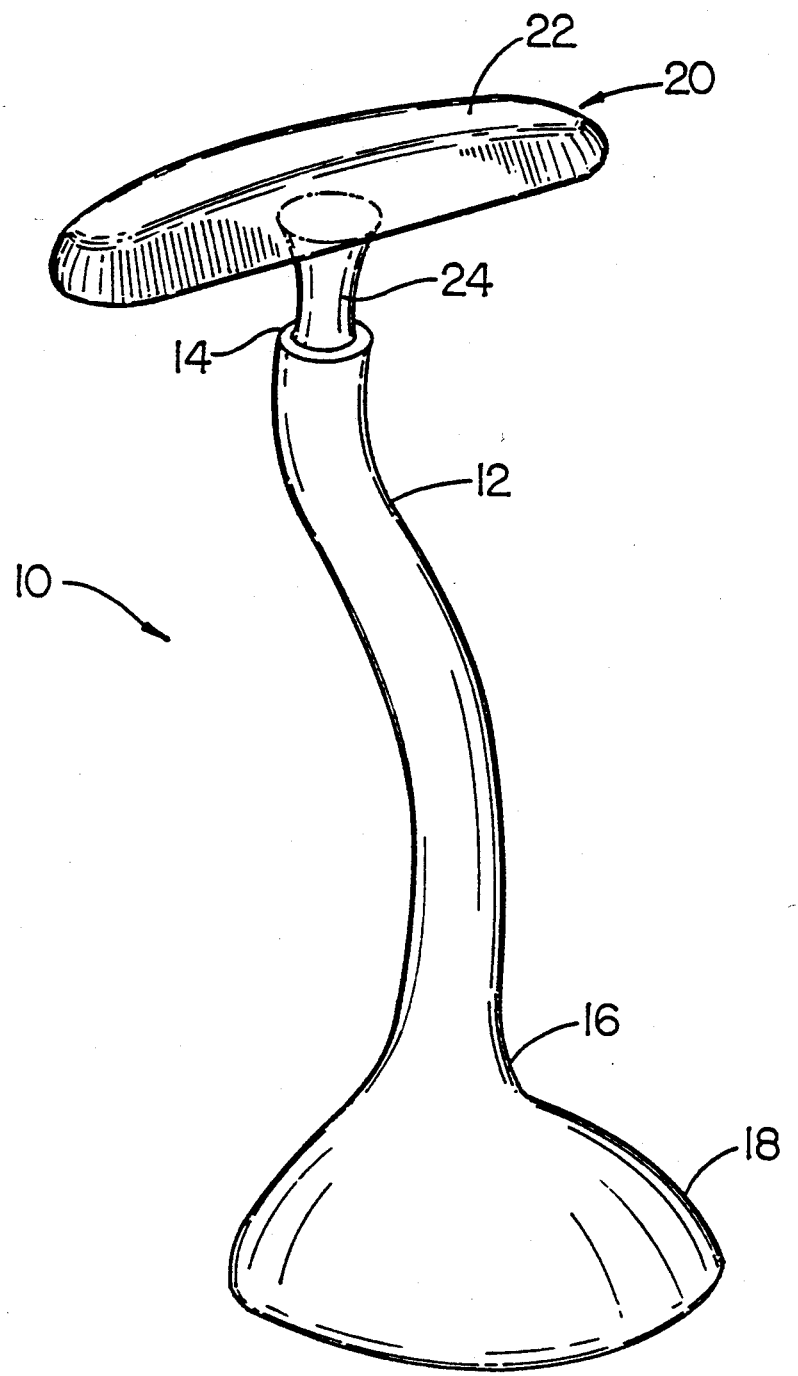
FIG. 1 is a schematic view of a first embodiment of the fixation stent of the invention.

Referring to FIG. 1, a first embodiment of the fixation stent of the invention is shown. In this embodiment, a fixation stent 10, comprises flexible tubing 12 having a proximal end 14 and a distal end 16. An inflatable portion, referred to as a balloon 18, is in fluid communication with the distal end 16 of the tube 12, and in the illustrated embodiment, is formed as an integral portion of the tubing 12, although it can also be a separate part attached to the distal end 16. A T-top plug 20 having a T-top 22 integral with a stem 24 is secured within the proximal end 14 of the tube 12.

The tubing 12, the balloon 18, and the plug 20, may be formed of any inert, non-toxic flexible and pliable material that is compatible with biological tissue. The preferred material is a medical grade silicone (polysiloxane) elastomer polymer, such as "SILASTIC" (Dow Corning Corp). Other suitable materials include silicone and polymethylmethacrylate (PMMA).

The tubing 12 may have an external diameter of generally 1.1 mm, and an internal diameter of generally 0.65 mm, for example. The balloon 18 may be generally a 0.5 cc–2.0 cc balloon, for example. The T-top 22 of plug 20 has a diameter which is greater than the diameter of the punctum (canalicular opening) of the eye, for example, about 0.8 mm. The length of the plug 20 may be approximately 1.5 mm, for example.

The T-top plug 20 may be secured within the proximal end 14 of the tubing 12 by friction as the outer diameter of the stem 24 is slightly greater than the inner diameter of tube 12. Friction attachment between the plug 20 and tube 12 may be enhanced by having ribs or threads located on the stem 24 of the plug 20. The plug 20 may also be secured within the tubing 20 using an adhesive. In this instance, the stem 24 of the plug 20 is dipped in a suitable glue such as cyanoacrylate glue, placed in the proximal end 14 of the tubing 12, and allowed to dry for a period of about 5 to 15 minutes.

Figure 2:
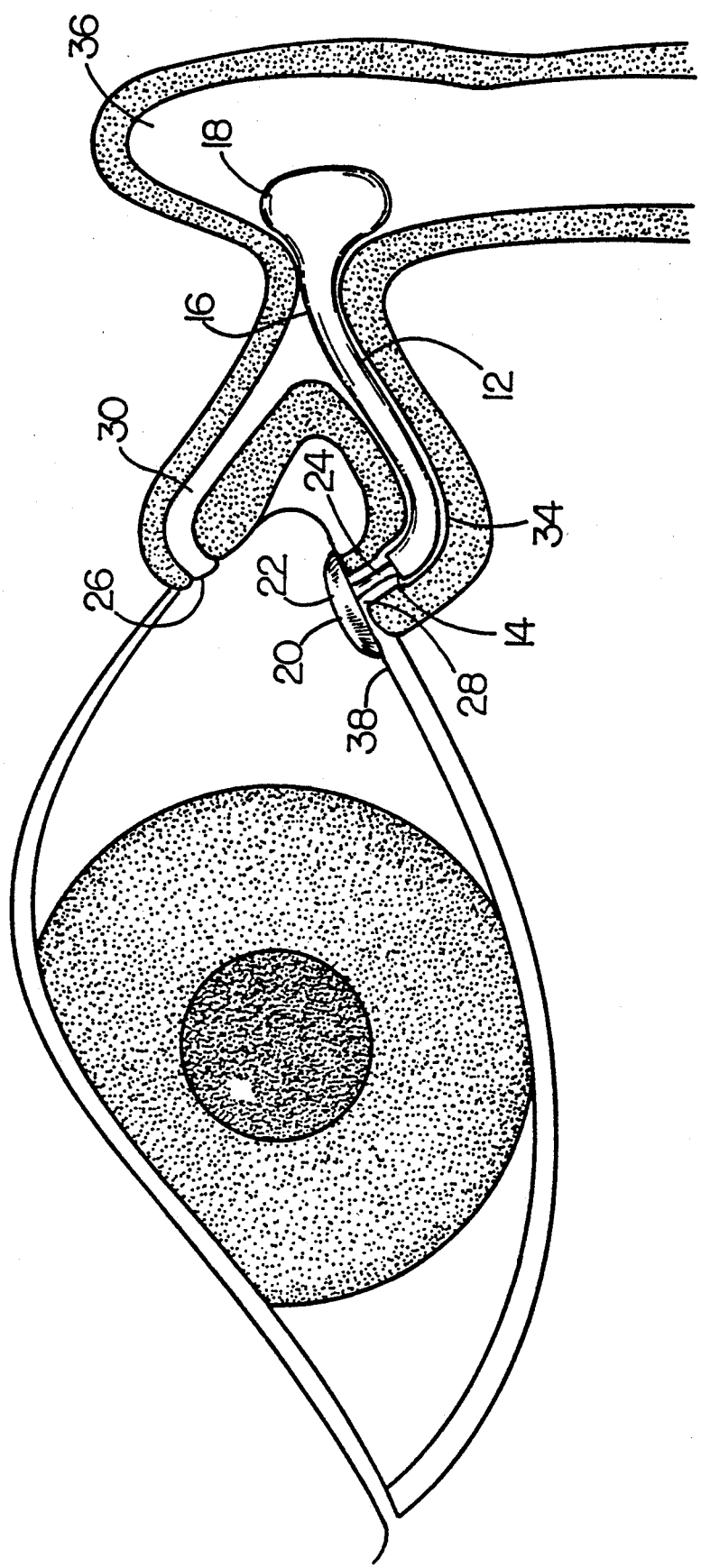
FIG. 2 is a schematic view of the first embodiment of the fixation stent implanted in a lacrimal outflow system of an eye.

With reference to FIG. 2, the first embodiment of the stent of the invention is shown placed within the lacrimal outflow system of an eye. The lacrimal outflow system includes the upper and lower punctae 26, 28 of the eye, and the upper and lower canaliculi (canals) 30, 34 which open to the lacrimal sac 36.

The lacrimal outflow system can easily be intubated with the fixation stent of the invention while the patient is under a local anesthetic. Intubation with the stent may be accomplished in any of several ways known in the art. In one method, a flexible blunted rod, such a 27 gauge or other suitably sized rod, is inserted within the tubing 12 after being lubricated with an ophthalmic ointment, and is used to feed the stent into the lacrimal outflow system.

As shown in FIG. 2, the distal end 16 of tubing 12 of the stent is fed through the lower punctum 28, and is urged through the lower lacrimal canal 34 to place the balloon 18 in the canalicular sac 36. The rod is then removed, the balloon 18 then being inflated via the proximal end 14 of the tubing 12 with a fluid such as air, saline, or silicone oil, for example, until the diameter of the balloon 18 exceeds the diameter of the lower canalicular canal 34. The tubing 12 is then clamped at the edge of the eyelid margin 38 with a small clamp just below the proximal end 14 of the tubing 12. The tubing 2 is then gently tugged to ascertain whether the inflated balloon is securely anchored in the lacrimal sac. The plug 20 is then secured within the proximal end 14 of the tubing 12. The plug 20 serves to seal the fluid used to inflate the balloon 18 within the tubing 12, as well as to anchor the proximal end 14 of the tubing at the margin of the eye. The clamp is then removed, and the T-top 22 of plug 20 is allowed to rest on the eyelid margin 38, thereby anchoring the proximal end 14 of the stent 10 at the eyelid margin 38.

After the stent is in place, canalicular laceration repair and reconstruction may proceed more easily, as is known in the art. Upon healing of the laceration repair, the canalicular stent can easily be removed by gently tugging on the T-top 22 of the plug 20 to expose the tubing 12 just below the plug 20. The tubing 12 is then cut or punctured just below the plug 20 to allow the balloon 18, anchored in the lacrimal sac 36, to be deflated. The entire stent is then removed from the lower canalicular canal 34 via the lower punctal opening 28.

If the stent of the invention is to be used to treat symptoms related to an unfavorable condition of the eye referred to as dry eye, the stent can remain in place for extended periods of time.

Figure 3:
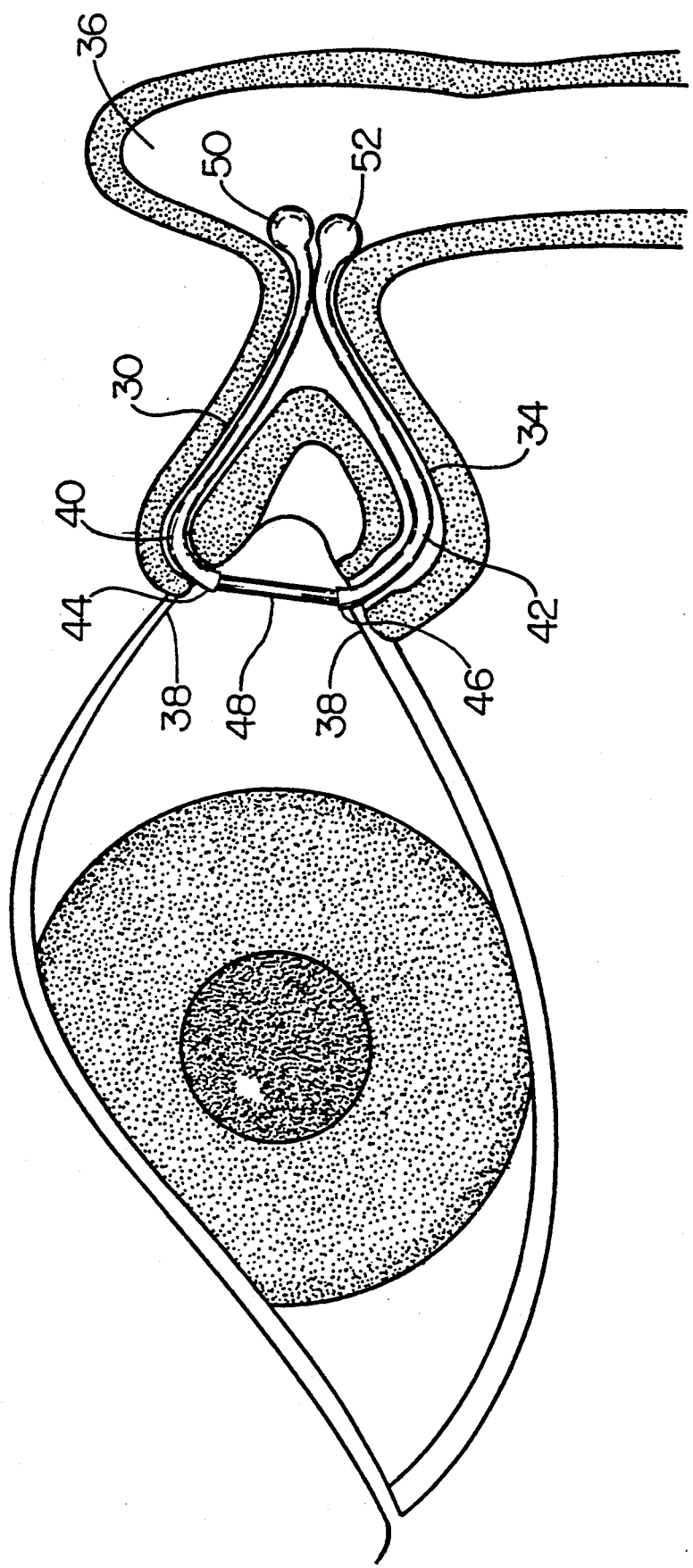
FIG. 3 is a schematic view of a second embodiment of the fixation stent implanted in a lacrimal outflow system of an eye.

In a second embodiment, a bicanalicular fixation stent can be used to intubate both the upper and the lower canalicular canals 30, 34. As shown in FIG. 3, the upper and lower canalicular canals 30, 34 are each separately intubated with first and second monocanalicular fixation stents 40, 42, each individual stent being substantially as described above, except that in this second embodiment, the opposite ends of a fixation rod 48 are secured within the respective proximal ends 44, 46 of the first and second monocanalicular fixation stents 40, 42 so as to connect the proximal ends 44, 46.

Subsequent to the insertion of each monocanalicular stent 40, 42, each stent is clamped at the lid margin 38 while the opposite ends of the fixation rod 48 are inserted in the respective proximal ends 44, 46 of each of the stents 40, 42. Once the clamps are removed, the fixation rod 48 serves to anchor the respective proximal ends 44, 46 at the margin 38 of the eyelid. The fixation rod 48 also functions to seal the respective proximate ends 44, 46 so as to retain the fluid within the inflated balloons 50, 52 of the respective first and second stents 40, 42, thereby trapping the inflated balloons 50, 52 within the lacrimal sac. The stents 40, 42 are thereby anchored within the lacrimal sac 36 via their respective inflated balloons 50, 52.

The fixation rod 48 may be made of a suitable medical grade material such as "SILASTIC", and may be secured within the respective proximal ends 44, 46 with an adhesive such as cyanoacrylate glue.

The bicanalicular balloon fixation stent of the second embodiment of the invention is particularly useful in those instances where both the upper and lower canalicular canals require repair or reconstruction, of when it is necessary to completely block the lacrimal outflow system of an eye to prevent the drainage of tears or opthalmic medications, as in cases of severe dry eye, for example.

The stent of the invention is not to be limited to use in canals associated with the eye, and can also be used in any narrow body canal, such as fallopian tubes, small veins and arteries, and lymph ducts.

Other modifications and implementations will occur to those skilled in the art without departing from the spirit and the scope of the invention as claimed. Accordingly, the above-description is not intended to limit the invention except as indicated in the following claims.

What is claimed is:

1. A fixation stent for insertion in a lacrimal canal, the stent comprising:
   a flexible tube having a proximal end, a distal end, and a hollow extending from the proximal end to the distal end, for transferring fluid therebetween;
   an inflatable portion, in fluid communication with the distal end of the tube, for expandably receiving the fluid, said inflatable portion, when uninflated, being of dimensions small enough to fit through a lacrimal canal and, when inflated, being of dimensions large enough to prevent exit through said lacrimal canal; and
   a plug secured to the proximal end of the tube, for anchoring the stent within the lacrimal canal and preventing the fluid from escaping via the proximal end of the tube.

2. The stent of claim 1 wherein the plug comprises:
   a stem sized for secure insertion into the proximal end of the tube; and
   a top, connected to the stem, having a diameter larger than the diameter of the body canal.

3. The stent of claim 1, wherein the plug is secured within the proximal end of the tube by friction.

4. The stent of claim 1 wherein the plug is secured in the proximal end by adhesive.

5. The stent of claim 1 wherein both the flexible tube and the plug are formed of an inert, non-toxic, medical grade polymer.

6. The stent of claim 5 wherein the medical grade polymer is selected from the group consisting of polysiloxane, silicone, and polymethylmethacrylate.

7. A bicanalicular fixation stent for treatment of medical conditions related to the eye, the stent comprising:

a first monocanalicular fixation stent including a first flexible tube having a first proximal end, a first distal end and a first inflatable portion in fluid communication with the first distal end;

a second monocanalicular fixation stent including a second flexible tube having a second proximal end, a second distal end and a second inflatable portion in fluid communication with the second distal end, wherein said first and second inflatable portions, when uninflated, are of dimensions small enough to fit, independently, through a lacrimal canal and, when inflated, are of dimensions large enough to prevent exit, independently, through said lacrimal canal; and a connector having first and second opposite ends, the first end being secured to the first proximal end of the first stent, and the second end being secured to the second proximal end of the second stent, so as to seal the first and second proximal ends, and to anchor each of the stents at the margin of the eyelid.

* * * * *

UNITED STATES PATENT AND TRADEMARK OFFICE
CERTIFICATE OF CORRECTION

PATENT NO. : 5,318,513
DATED : June 7, 1994
INVENTOR(S) : Martin L. Leib, et al.

It is certified that error appears in the above-indentified patent and that said Letters Patent is hereby corrected as shown below:

Column 2, line 2,
On the cover page, after Attorney, Agent, or firm, "Gagnerbin" should read --Gagnebin--.

Title page, item [57],
In the Abstract, line 11, "canaliculus Once" should read --canaliculus. Once--.

In the Abstract, line 17, "stent The" should read --stent. The--.

In the Abstract, line 21, "eyelid Although" should read --eyelid. Although--.

Column 3, line 43, "2 is" should read --12 is--.

Column 4, line 32, "of when" should read --or when--.

Signed and Sealed this

Third Day of January, 1995

Attest:

BRUCE LEHMAN

Attesting Officer     *Commissioner of Patents and Trademarks*